United States Patent
Edge et al.

(10) Patent No.: US 10,139,358 B2
(45) Date of Patent: Nov. 27, 2018

(54) METHOD FOR CHARACTERIZATION OF A LAYERED STRUCTURE

(71) Applicants: International Business Machines Corporation, Armonk, NY (US); GlobalFoundries, Inc., Grand Cayman (KY)

(72) Inventors: Lisa F. Edge, Westlake Village, CA (US); Gangadhara R. Muthinti, Albany, NY (US); Shariq Siddiqui, Albany, NY (US)

(73) Assignees: INTERNATIONAL BUSINESS MACHINES CORPORATION, Armonk, NY (US); GLOBALFOUNDRIES INC., Grand Cayman (KY)

( * ) Notice: Subject to any disclaimer, the term of this patent is extended or adjusted under 35 U.S.C. 154(b) by 237 days.

(21) Appl. No.: 14/992,319

(22) Filed: Jan. 11, 2016

(65) Prior Publication Data
US 2017/0199139 A1    Jul. 13, 2017

(51) Int. Cl.
*G01N 21/21* (2006.01)
*G01N 27/02* (2006.01)
*G01N 21/25* (2006.01)

(52) U.S. Cl.
CPC .............. *G01N 27/02* (2013.01); *G01N 21/25* (2013.01)

(58) Field of Classification Search
CPC .................................. G01N 27/02; G01N 21/25
See application file for complete search history.

(56) References Cited

U.S. PATENT DOCUMENTS

| 4,195,892 A | * | 4/1980 | Riley | H01J 9/241 29/413 |
| 4,706,018 A | * | 11/1987 | Beha | G01R 31/308 324/754.23 |

(Continued)

FOREIGN PATENT DOCUMENTS

JP     5785571 B2    9/2015

OTHER PUBLICATIONS

Bender et al.; "Physical Characterisation of High-k Gate Stacks Deposited on HF—Last Surgaces"; IWGI 2001, Tokyo; pp. 86-92.
(Continued)

*Primary Examiner* — Laura Menz
(74) *Attorney, Agent, or Firm* — Cantor Colburn LLP; Steven Meyers

(57) ABSTRACT

In an embodiment, a method comprises fitting a spectroscopic data of a layer in a layered structure to a dielectric function having a real part and an imaginary part; confirming that the dielectric function is physically possible; based on the dielectric function not being physically possible, repeating the fitting the spectroscopic data, or, based on the dielectric function being physically possible, defining an n degree polynomial to the dielectric function; determining a second derivative and a third derivative of the n degree polynomial; equating the second derivative to a first governing equation and the third derivative to a second governing equation and determining a constant of the first governing equation and the second governing equation; and based on the key governing equations, determining one or more of a band gap, a thickness, and a concentration of the layer.

20 Claims, 5 Drawing Sheets

(56) References Cited

U.S. PATENT DOCUMENTS

| | | | |
|---|---|---|---|
| 5,255,070 A | 10/1993 | Pollak et al. | |
| 6,381,009 B1* | 4/2002 | McGahan | G01B 11/0641 356/369 |
| 6,583,876 B2 | 6/2003 | Opsal et al. | |
| 6,646,752 B2 | 11/2003 | Chen et al. | |
| 8,324,011 B2* | 12/2012 | Poon | H01L 21/324 257/E21.324 |
| 8,756,540 B1* | 6/2014 | Baeckler | G06F 17/505 716/101 |
| 8,990,759 B2 | 3/2015 | Aghababazadeh et al. | |
| 9,347,872 B1* | 5/2016 | Poslavsky | G01N 21/211 |
| 9,405,290 B1* | 8/2016 | Malkova | H01L 21/00 |
| 9,595,481 B1* | 3/2017 | Malkova | H01L 22/12 |
| 9,721,055 B2* | 8/2017 | Pandev | G06F 17/5081 |
| 2002/0180991 A1* | 12/2002 | Takoudis | G01N 21/3563 356/630 |
| 2013/0083320 A1* | 4/2013 | Gao | G01N 21/9501 356/237.5 |
| 2013/0132021 A1* | 5/2013 | Kwak | G01N 21/274 702/104 |
| 2013/0245985 A1* | 9/2013 | Flock | G03F 7/70625 702/105 |
| 2013/0304408 A1* | 11/2013 | Pandev | H01L 22/20 702/83 |
| 2013/0305206 A1* | 11/2013 | Pandev | G06F 17/5081 716/136 |
| 2013/0321810 A1* | 12/2013 | Wang | G03F 7/70625 356/369 |
| 2014/0172394 A1* | 6/2014 | Kuznetsov | G06F 17/5009 703/6 |
| 2014/0297211 A1* | 10/2014 | Pandev | G03F 7/70558 702/81 |
| 2014/0316730 A1* | 10/2014 | Shchegrov | H01L 22/12 702/81 |
| 2014/0340682 A1* | 11/2014 | Kwak | G01N 21/211 356/369 |
| 2014/0347666 A1* | 11/2014 | Veldman | G01N 21/211 356/369 |
| 2015/0176985 A1* | 6/2015 | Shchegrov | H01L 22/12 356/614 |
| 2016/0282105 A1* | 9/2016 | Pandev | G01B 11/0616 |
| 2016/0341792 A1* | 11/2016 | Malkova | G01R 31/308 |
| 2017/0023491 A1* | 1/2017 | Cao | G01N 21/211 |
| 2017/0199139 A1* | 7/2017 | Edge | G01N 27/02 |

OTHER PUBLICATIONS

Campera et al.; "Modeling of Tunnelling Currents in Hf-Based Gate Stacks as a Function of Temperature and Extraction of Material Parameters"; IEEE Transactions on Electron Devices, vol. 54; No. 1; Jan. 2007; pp. 83-89.

Cho et a; "Ellipsometric determination of optical properties for ultrathin gate oxides"; 1999; IEEE; pp. 957-958.

Li et al.; "A Program for Device Model Parameter Extraction from Gate Capacitance and Current of Ultrathin SiO2 and High-k Gate Stacks"; IEEE Transactions on electron Devices; vol. 53; No. 9; Sep. 2006; pp. 2118-2127.

Ocker et al.; "Characterization of Multilayer Gate Stacks by Multi-Phonon Transient Trap Spectroscopy"; 2013; IEEE; pp. 1-4.

Price et al.; "Characterization of sub-nm AlOx and LaOx capping layers on high-k gate stack film systems using VuV reflectivity"; 2010; IEEE; pp. 86-87.

Zapien et al.; "Real time characterization of wide band gap think film growth using uv-extended spectroscopic ellipsometry: application to cubic boron nitride"; 2001; IEEE; pp. 67-69.

M. Ruzi, et al., "Spectral Curve Fitting of Dielectric Constants", AIP Advances 7, 015042 (2017), 14 pages.

Mike Lanagan, "Dielectric Properties and Metamaterials", 2008, US—Japan Winter School on New Functionality in Glass, Kyoto, Japan, 73 pages.

Paul Ehrlich, "A Simple Calculation of Dielectric Loss from Dielectric Dispersion for Polar Polymers", Journal of Research of the National Bureau of Standards • vol. 50, No. 1, Jan. 1953, Research Paper 2382.

* cited by examiner

METHOD FOR CHARACTERIZATION OF A LAYERED STRUCTURE

BACKGROUND

The present invention relates to a method for characterization of a layered structure, specifically, of a gate stack for fabrication of high mobility channel semiconductor devices.

Semiconductor components, such as microprocessors are formed from high-density integrated circuits (ICs). Semiconductor device fabrication is a multi-step and complex process consisting of numerous steps, where each process step requires the use of ultra-sensitive machinery and techniques. The formed semiconductor device can be quality tested after the completion of the fabrication sequence, where full-wafer functional test and/or specific circuits of the device are performance-tested under pre-determined operating conditions. Waiting to test the semiconductor device until after completion of the fabrication process does not allow for determination of where in the fabrication process a failure occurred. Accordingly, as the semiconductor fabrication is so complex, it is often desirable to monitor the quality of the wafer at various times during the fabrication process. Therefore, if problems such as defects and/or process excursions are encountered in the fabrication and detected quickly, the fabricator can take remedial action.

Wafer quality during the fabrication process can be monitored by measuring certain parameters that can be indicative of possible problems or unanticipated outcomes from the fabrication process. These parameters can be monitored, for example, by means of optical and electron beam techniques. In one approach, measurements are made to verify certain physical parameters such as gate width, gate-oxide thickness, interconnect width, and dielectric height. Under such an approach, the measurements can be made on test structures in the wafer scribe area, adjacent to the active portion of the chips.

A further approach uses electrical testing of specialized test structures positioned in a scribe portion of the wafer that will not be used in the final product.

As semiconductor devices are constantly decreasing in size and are becoming increasingly complex, improved methods to monitor the fabrication process are desired.

SUMMARY

According to an embodiment of the present invention, a method comprises fitting a spectroscopic data of a layer in a layered structure to a dielectric function having a real part and an imaginary part; confirming that the dielectric function is physically possible; based on the dielectric function not being physically possible, repeating the fitting the spectroscopic data, or, based on the dielectric function being physically possible, defining an n degree polynomial to the dielectric function; determining a second derivative and a third derivative of the n degree polynomial; equating the second derivative to a first governing equation and the third derivative to a second governing equation and determining a constant of the first governing equation and the second governing equation; and based on the key governing equations, determining one or more of a band gap, a thickness, and a concentration of the layer.

According to an embodiment of the present invention, a system comprises an illuminator that is operative to illuminate a layered structure over a spectral range to form an illuminated layered structure; a spectrometer that is operative to measure spectroscopic data from the illuminated layered structure; and a computer system configured to: receive the spectroscopic data from the spectrometer; fit the spectroscopic data of a layer of the layered structure to a dielectric function having a real part and an imaginary part; confirm that the dielectric function is physically possible; based on the dielectric function being physically possible, define an n degree polynomial to the dielectric function; determine a second derivative and a third derivative of the n degree polynomial; equate the second derivative to a first governing equation and equate the third derivative to a second governing equation; and determine a constant of the first governing equation and the second governing equation; based on one or both of the first governing equation and the second governing equation, determine one or more of a band gap, a thickness, and a concentration of the layer.

According to an embodiment of the present invention, a computer program product comprising a computer readable storage medium having program instructions embodied therewith, the program instructions executable by a processor to cause the processor to perform a method comprises fitting a spectroscopic data of a layer in a layered structure to a dielectric function having a real part and an imaginary part; confirming that the dielectric function is physically possible; based on the dielectric function not being physically possible, repeating the fitting the spectroscopic data, or, based on the dielectric function being physically possible, defining an n degree polynomial to the dielectric function; determining a second derivative and a third derivative of the n degree polynomial; equating the second derivative to a first governing equation and the third derivative to a second governing equation and determining a constant of the first governing equation and the second governing equation; and based on the key governing equations, determining one or more of a band gap, a thickness, and a concentration of the layer.

BRIEF DESCRIPTION OF THE DRAWINGS

Refer now to the figures, which are exemplary embodiments, and wherein the like elements are numbered alike.

DETAILED DESCRIPTION

Figure 1:
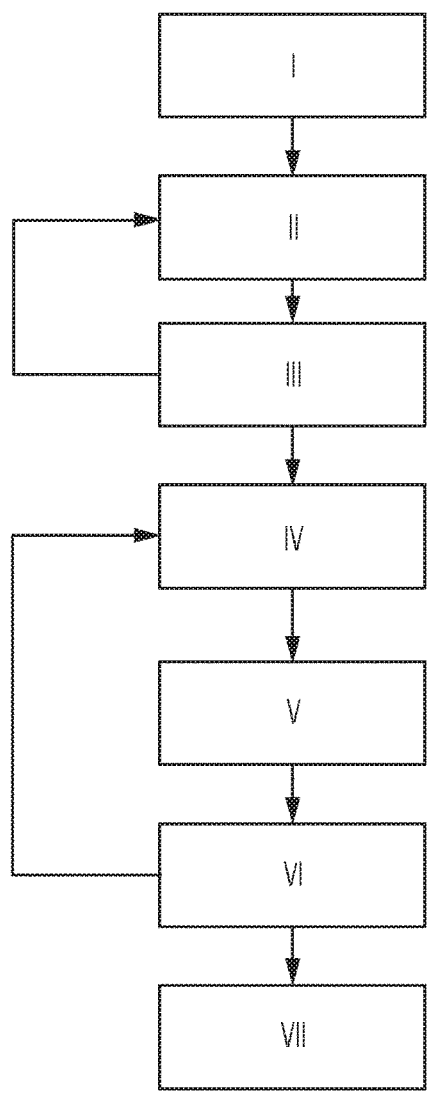
FIG. 1 is an illustration of a method of determining the physical parameters of a layered structure.

The scaling of the gate stack has been a key to enhancing the performance of complementary metal-oxide-semiconductor (CMOS) field-effect transistors (FETs) of past technology generations. The precise measurement during fabrication of various parameters of the layers in the gate stack is important in being able to predict the viability of the final semiconductor device. For example, the band structure characteristic (for example, band gap, band edge, energy band defects, band broadening, and the like) can contribute to unintended leakage of current through a high dielectric constant layer of a finished wafer. Hence, information such as band gap determined in an unfinished semiconductor device can be an indicator of electrical performance of the finished semiconductor device.

An analytical method was therefore determined to characterize one or more parameters in a layered structure, for example, in a gate stack that can help to identify whether the resulting semiconductor will have the electrical properties needed for its intended use. The method comprises collecting physical data from a layered structure, fitting the data to a model by defining a dielectric function, defining a polynomial, and fitting a second and third derivative of the polynomial to a first and second key governing equation. The resulting key governing equations can provide physical properties such as the thickness of the respective layers, the band gap, the strain in the silicon germanium layer, and the germanium concentration in the silicon germanium layer.

The method can determine the thickness of each of the layers to plus or minus 3 Angstroms, specifically, to plus or minus 2 Angstroms. This accuracy in determining layer thickness allows for a more accurate prediction in determining the future performance of the semiconductor device. The ability to determine the physical properties of the layered structure is beneficial as a sacrificial wafer that might otherwise have to be prepared to determine layer thickness by destructive techniques such as transmission electron microscopy can be avoided. In this manner, without even destroying the wafer, the thickness of all of the layers simultaneously can be readily determined.

The method also allows for the determination of the band gap, for example, to at least two decimal places for one or more layers in the layered structure. For example, the method can determine the band gap for both an oxide layer and a high dielectric constant layer in a gate stack, where a shift in the band gap, which represents the energy at which the respective layer starts absorbing light, is directly related to the quality of the layer. Determining the band gap can provide information about the quality of the formed layers, where a better quality indicates a better performance of the resultant semiconductor device.

This method of analyzing a layered structure can be beneficial in a gate stack comprising one or both of a silicon germanium layer and a high dielectric constant material layer. For example, in the manufacture of a gate stack comprising a silicon germanium layer, the presence of the germanium imposes a biaxial strain in the silicon germanium layer and can ultimately impose a strain on surrounding layers. The amount of strain imposed can have an effect on the functioning of the final product. Accordingly, the precise monitoring of one or more of the thickness of the silicon germanium layer, the amount of germanium deposited, and the strain associated with the silicon germanium layer can help to identify whether the resulting semiconductor will have the electrical properties needed for its intended use.

Furthermore, in the manufacture of a gate stack comprising a high dielectric constant material layer, an early determination of a deposition problem can be important from a cost saving standpoint as these materials can be expensive and the deposition time can be lengthy, for example, taking weeks to manufacture. Prior techniques for analyzing a gate stack comprise shining a light on the gate stack; collecting the reflectivity of the data; and analyzing the data to get the thickness data. These methods are limited in the amount of information that can be withdrawn.

The method of analyzing a layered structure can comprise fitting spectroscopic data of a layer in the layered structure to a dielectric function having a real part and an imaginary part; confirming that the dielectric function is physically possible; based on the dielectric function being physically possible, defining an n degree polynomial to the dielectric function; determining a second derivative and a third derivative of the n degree polynomial; equating the second derivative to a first governing equation and the third derivative to a second governing equation and determining the constants of the first governing equation and the second governing equation; and based on the key governing equations, determining one or more of a band gap, a thickness, and a concentration of the layer. The method can determine one or more of respective layer thickness, band gap, and layer concentration (for example, of a dopant), where one or more of these data can be indicative of the future performance of the semiconductor device.

FIG. 1 is an illustration of an embodiment of the method of analyzing the layered structure.

Step I comprises collecting physical data from a layered structure. The data can be collected using a spectroscopic technique such as ultraviolet-visible-infrared spectroscopy or ellipsometry. The data can be collected without normalization to a reference material.

Step II comprises defining a dielectric function for each layer in the stack. For example, Step II can comprise fitting the experimental data, for example, of the amplitude ratio ($\Psi$) and the total phase shift ($\Delta$) over the range of photon energy to one or more dielectric functions depending on the desired number of layers to be analyzed. The dielectric functions can be determined by inputting values such as a proposed layer thickness, a proposed band gap, and the dielectric information; comparing the resultant dielectric function to the data; and iterating the input values until the dielectric function matches the data.

The dielectric functions are functions of the wavelength (s) used in Step I, where the dielectric functions have a real part ($\varepsilon_1$) and an imaginary part ($\varepsilon_2$). For example, a dielectric function for a given wavelength can have the formula (I).

$$\varepsilon = \varepsilon_1 + i\varepsilon_2 \quad \text{(I)}$$

Step III comprises confirming that the dielectric functions determined are physically possible and that the resulting thickness values are real numbers. If at least one of the dielectric functions determined is not physically possible and the resulting thickness value is not a real number, then Step II is repeated for that dielectric function.

If one or more dielectric functions cannot be determined to match the data, then the data can be smoothened, for example, by data averaging and Step II can be repeated. A data smoothening step can be used, for example, if the data has a low signal-to-noise ratio.

Step IV comprises defining an n degree polynomial based on the dielectric functions determined in Step II. Defining the n degree polynomial can help to smoothen the data.

Step V comprises calculating the first, second, and third differential equations for the polynomial equation determined in Step IV. It was surprisingly found that by utilizing high order polynomial smoothening of the data, an improvement in the accuracy of the data could be achieved, for example, as compared to techniques utilizing Fourier transforms.

Step VI comprises performing a critical point analysis on the second and third differential equations using a regression model to fit the second and third differential equations to the key governing equations; and determining the constants of the equations. The key governing equations fit to the second and third derivatives can have the formulae (II) and (III), $$\frac{d^2s}{dE^2} = \sum_{j=i}^{3} n(n-1)A_j e^{i\varphi j}(E - E_j + i\Gamma_j)^{n-2} \quad \text{(II)}$$

$$\frac{d^3(\varepsilon E^2)}{dE^3} = \sum_{j=1}^{3} C_j e^{i\varphi j}(E - E_j + i\Gamma_j)^{-4+n/2} \quad \text{(III)}$$

where n is the critical point, $\varphi_j$ is the phase angle of the $j^{th}$ critical point, $C_j$ is the scaling factor of the $j^{th}$ critical point, $\Gamma_j$ is the broadening energy of the $j^{th}$ critical point, and $E_j$ is the transition energy of the $j^{th}$ critical point.

After determining the constants of the key governing equations, the constants can be checked for physicality. If the constants are not physically possible, then the data can be further smoothened, for example, by increasing the degree of the polynomial and repeating steps IV-VI.

Step VII comprises reporting such information as the optical band gap, the complex index of refraction (such as a real (n) and imaginary (k) part thereof), layer thicknesses for each layer, a layer concentration (for example, a germanium concentration in the silicon germanium layer), a square root of $\in_2$, an absorption constant, an attenuation constant, a layer stress, a layer strain, and the like.

The present method can be used to determine the layer properties of a layered structure comprising two or more layers, specifically, 2 to 10 layers, more specifically, 2 to 4 layers. Examples of layers in the layered structure can be a semiconductor layer, an oxide layer, a high dielectric constant layer, a carbon layer (such as a graphene layer), and the like.

The method for analyzing the layered structure can be performed using a system comprising an illuminator that can illuminate the layered structure over a spectral range to form an illuminated layered structure; a spectrometer that can measure spectroscopic data from the illuminated layered structure; and a computer system configured to receive and analyze the data from the spectrometer.

The computer system can comprise a non-transitory computer readable medium, for example, that can be implemented in hardware, software, firmware, or a combination comprising at least one of the foregoing. If implemented in software, the functions can be stored on or transmitted over as one or more instructions or code on a computer-readable medium. Computer-readable media can include a computer storage media and communication media including a medium that facilitates transfer of a computer program from one place to another.

Figure 2:
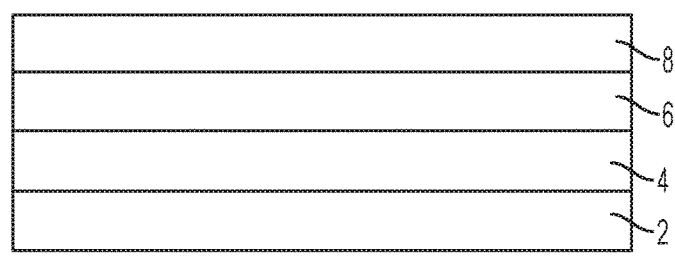
FIG. 2 is an illustration of an embodiment of a gate stack material.

The layered structure can be a gate stack. An example of a gate stack is illustrated in FIG. 2. Specifically, FIG. 2 illustrates that the gate stack can comprise substrate layer 2, semiconductor layer 4, oxide layer 6, and high dielectric constant layer 8. Semiconductor layer 4 can be located in between substrate layer 2 and oxide layer 6. Oxide layer 6 can be located between semiconductor layer 4 and high dielectric constant layer 8.

Substrate layer 2 can comprise silicon and can be, for example, a silicon wafer. Substrate layer 2 can comprise gallium arsenide. Substrate layer 2 can comprise bulk silicon. Substrate layer 2 can comprise a semiconductor-on-insulator (such as silicon-on-insulator). Substrate layer 2 can comprise a Group III to Group V metal.

Semiconductor layer 4 can comprise silicon (Si), strained silicon, silicon carbide (SiC, germanium (Ge), silicon germanium (SiGe), silicon-germanium-carbon (SiGeC), a silicon alloy, a germanium alloy, gallium arsenide (GaAs), indium arsenide (InAs), indium phosphide (InP), cadmium arsenide, cadmium selenide, or a combination comprising at least one of the foregoing.

Semiconductor layer 4 can comprise silicon and germanium. The presence of the germanium can result in a gate stack with a high electron and hole mobility. For example, a gate stack comprising a silicon germanium layer can have a bulk hole mobility that is about four times higher than that of a pure silicon layer. This increased mobility results in an increase in channel drive current for a given device design and ultimately in improved performance.

Semiconductor layer 4 can be grown using a suitable growth process, for example, chemical vapor deposition (CVD), liquid phase (LP) chemical vapor deposition, reduced pressure chemical vapor deposition (RPCVD), vapor-phase epitaxy (VPE), molecular-beam epitaxy (MBE), liquid-phase epitaxy (LPE), metal organic chemical vapor deposition (MOCVD), or other suitable processes. Semiconductor layer 4 can be formed by epitaxial growth of the silicon germanium layer on the silicon layer. The epitaxial growth of the silicon germanium layer can comprise epitaxial growth of a polysilicon doped with germanium.

The germanium can be present in an amount of 5 to 40 atomic percent based on the total atoms in the silicon germanium layer. The germanium can be present in an amount of 20 to 80 weight percent (wt %), specifically, 10 to 60 weight percent based on the total weight in the silicon germanium layer of germanium based on the total weight of the layer. Semiconductor layer 4 can have a thickness of 80 to 200 Angstroms, specifically, 100 to 150 Angstroms.

Oxide layer 6 can comprise silicon dioxide ($SiO_2$), $Si_xGe_{1-x}O_y$, silicon oxy nitride ($SiO_xN_y$), or a combination comprising at least one of the foregoing. Oxide layer 6 can have a thickness of 5 to 20 Angstroms, specifically, 10 to 15 Angstroms or 5 to 8 Angstroms.

High dielectric constant layer 8 can comprise a high dielectric constant material. High dielectric constant layer 8 can comprise a material with one or both of a higher dielectric constant and a lower extinction coefficient than silicon dioxide. The presence of the high dielectric constant material can reduce leakage current and enable the manufacture of smaller sized transistors. High dielectric constant layer 8 can comprise silicon nitride ($Si_3N_4$), hafnium dioxide ($HfO_2$), hafnium tantalum titanium oxide (HfTaTiO), hafnium silicate ($HfSiO_4$), nitrided hafnium silicates (HfSiON), hafnium dioxide ($HfO_2$), zirconium dioxide ($ZrO_2$), zirconium silicate ($ZrSiO_4$), aluminum oxide ($Al_2O_3$), germanium oxynitride ($GeO_xN_y$), or a combination comprising at least one of the foregoing. High dielectric constant layer 8 can have a thickness of 5 to 50 Angstroms, specifically, 10 to 20 Angstroms.

The following examples are provided to illustrate method for characterizing a gate stack. The examples are merely illustrative and are not intended to limit devices or the method in accordance with the disclosure to the materials, conditions, or process parameters set forth therein.

EXAMPLES

Example 1: Characterization of the Band Gap, the Dielectric Function, and the Thickness of a Gate Stack A gate stack was prepared by depositing a silicon germanium layer on a 1 millimeter (mm) thick silicon wafer; forming an oxide layer of silicon dioxide on the silicon germanium layer; and forming a high dielectric constant layer of hafnium dioxide on the silicon dioxide layer.

The gate stack was analyzed using ellipsometry and the data was used to determine a dielectric function for each layer by first fitting the data to the dielectric function, fitting the dielectric function to a polynomial equation, and determining the key governing questions based on the second and third derivatives of the polynomial function.

Figure 3:
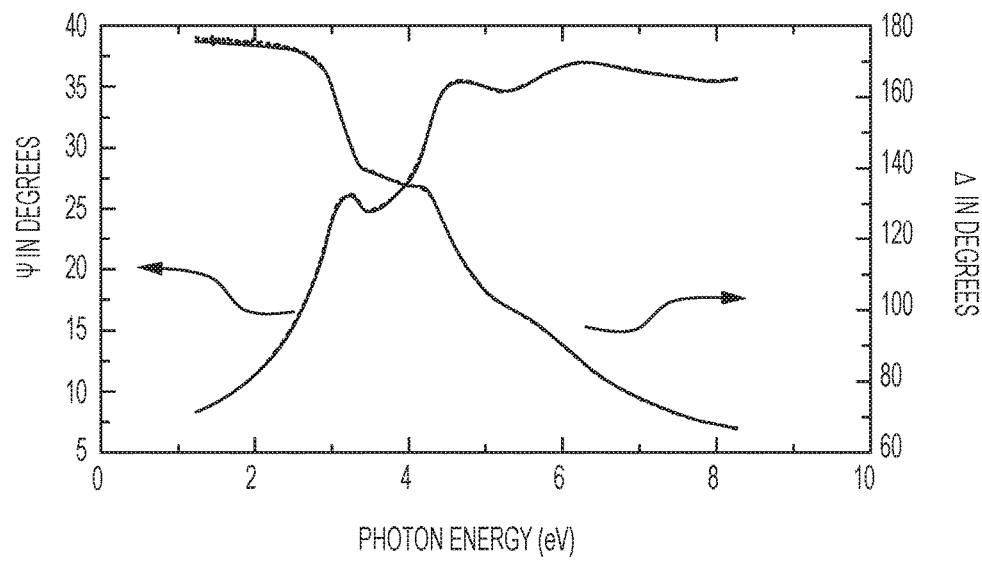
FIG. 3 is a graphical illustration of a model fit of the experimental data of Example 1 versus photon energy.

The resulting fit is illustrated in FIG. 3, where FIG. 3 illustrates that the model fit (solid lines) almost completely overlay the experimental data (dashed lines) for both Ψ and Δ over the range of photon energy, where Ψ is the amplitude attenuation and Δ is the total phase shift.

Figure 4:
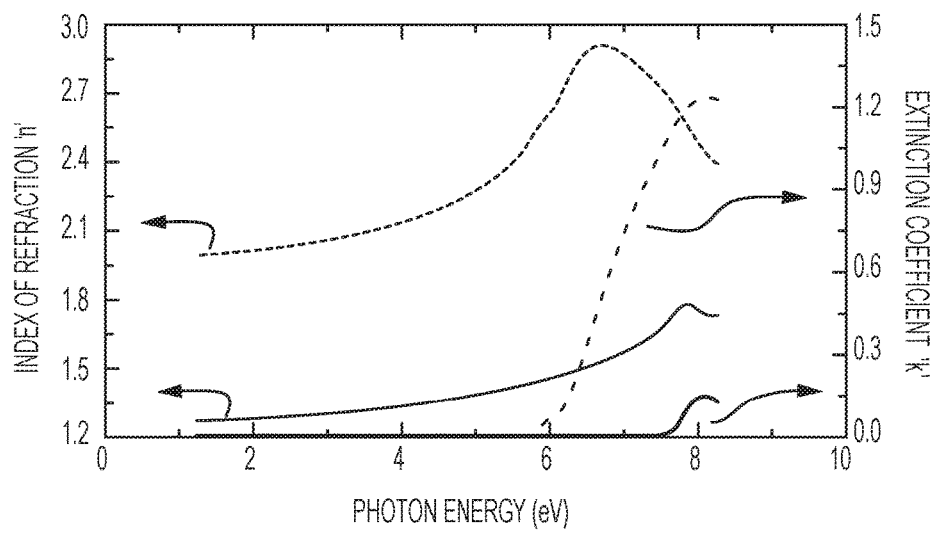
FIG. 4 is a graphical illustration of the index of refraction and the extinction coefficient for both the oxide layer and the high dielectric constant layer of Example 1 versus photon energy.

Based on the model fit, FIG. 4 illustrates that index of refraction n' and the extinction coefficient k' for both the oxide layer (solid lines) and the high dielectric constant layer (dashed lines).

Figure 5:
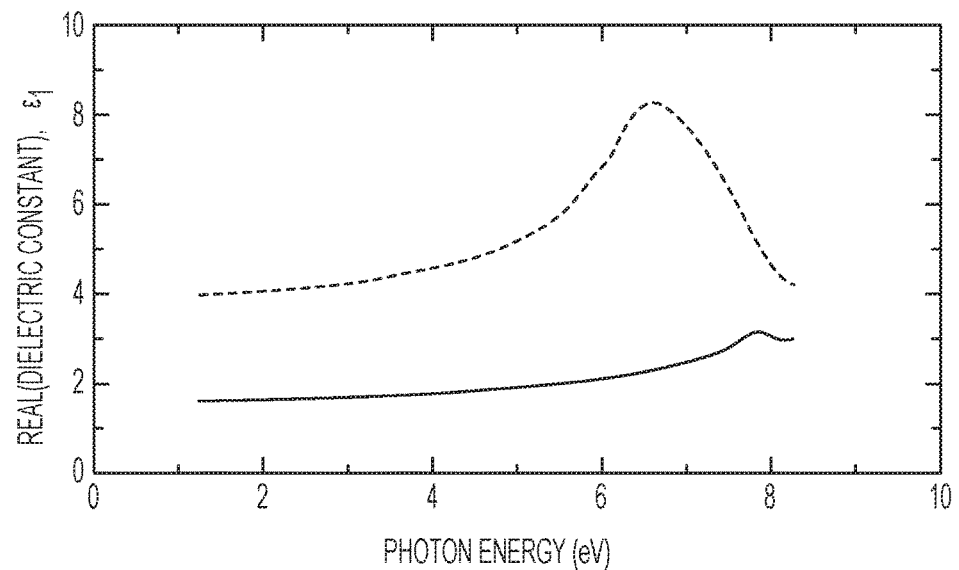
FIG. 5 is a graphical illustration of the real part of the dielectric constant for the oxide layer and the high dielectric constant layer of Example 1 versus photon energy.
Figure 6:
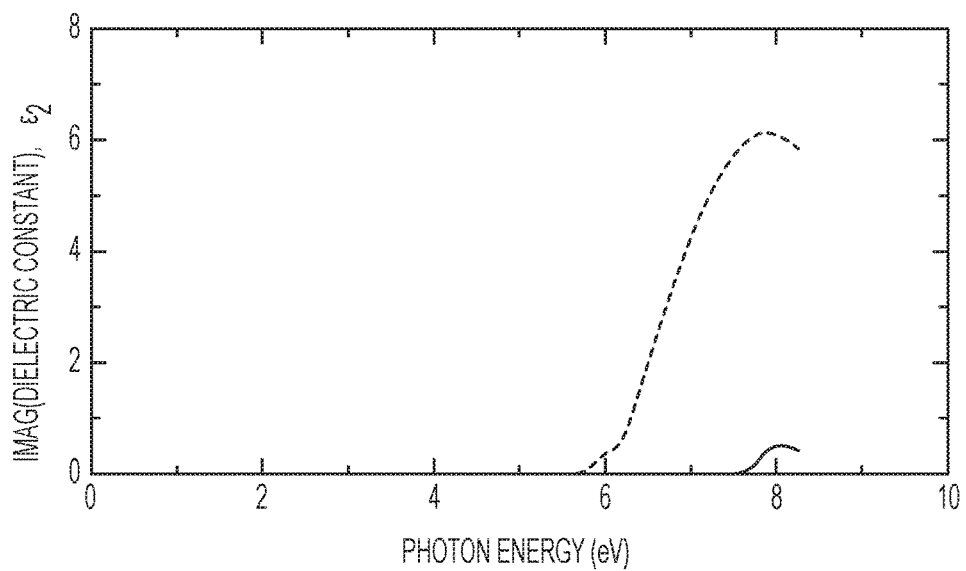
FIG. 6 is a graphical illustration of the imaginary part of the dielectric constant for the oxide layer and the high dielectric constant layer of Example 1 versus photon energy.

FIG. 5 is a graphical illustration of the real part of the dielectric constant for the oxide layer and the high dielectric constant layer versus photon energy in electron volts (eV). FIG. 6 is a graphical illustration of the imaginary part of the dielectric constant for the oxide layer and the high dielectric constant layer versus photon energy in electron volts. In FIG. 5 and FIG. 6, the solid line represents the oxide layer and the dashed line represents the high dielectric constant layer. FIG. 6 illustrates that the band gap for the oxide layer is 7.51 eV and the band gap for the high dielectric constant layer is 6.16 eV.

Based on the dielectric functions, the thickness of the silicon germanium layer was determined to be 140 Angstroms, the thickness of the oxide layer was determined to be 12 Angstroms, and the thickness of the high dielectric constant layer was determined to be 15 Angstroms. These thickness values were verified using cross-section transmission electron microscopy.

Example 2: Characterization of the Band Gap and the Dielectric Function Based on Differing Processing Conditions During the Preparation of a Gate Stack In Example 2, Gate Stacks A-E were prepared by depositing a silicon germanium layer on a 1 millimeter (mm) thick silicon wafer; forming an oxide layer of silicon dioxide on the silicon germanium layer; and forming a high dielectric constant layer of hafnium oxide on the silicon dioxide layer by varying the processing conditions during deposition of the high dielectric constant layer as shown in Table 1. In Table 1 nitridation refers to nitrogen being present in the chamber during the deposition of the high dielectric constant layer.

TABLE 1

|  | Gate Stack | | | | |
| --- | --- | --- | --- | --- | --- |
|  | A | B | C | D | E |
| Deposition temperature (° C.) | 700 | 700 | 700 | 600 | 300 |
| Post-deposition anneal | Yes | Yes | Yes | Yes | No |
| Nitridation | No | No | Yes | No | No |
| Reliability anneal at 950° C. | No | Yes | No | No | No |

Figure 7:
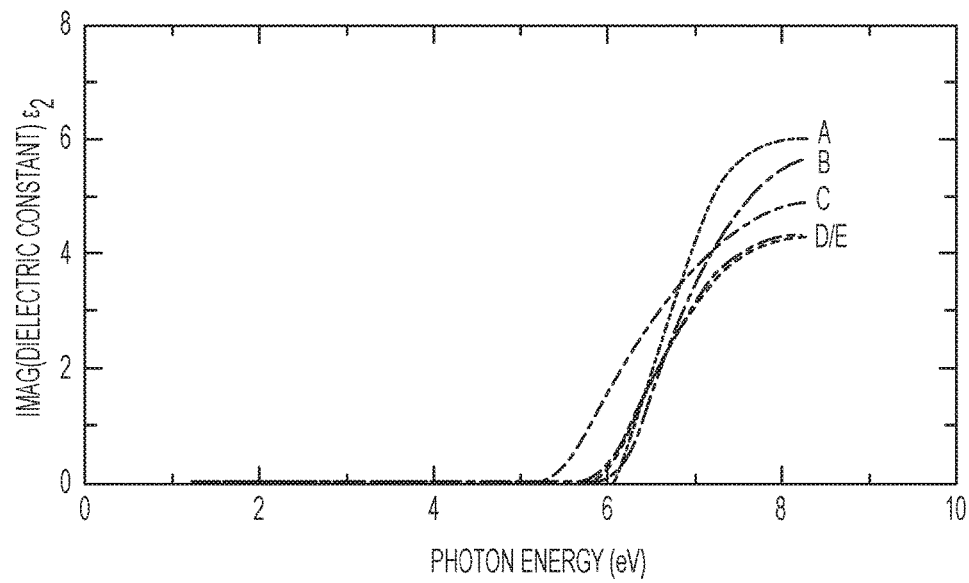
FIG. 7 is a graphical illustration of the imaginary part of the dielectric constant for the high dielectric constant layers of Example 2 versus photon energy.

The resultant imaginary part of the dielectric function of the high dielectric constant layer for Gate Stacks A-E are illustrated in FIG. 7. FIG. 7 illustrates that changes in the process and the quality of a process step can be easily identified using the present method.

Example 3: Effect of Germanium Concentration in the Silicon Germanium Layer on the Dielectric Function Gate Stacks F-H were prepared by depositing a silicon germanium layer on a 1 millimeter (mm) thick silicon wafer; forming an oxide layer of silicon dioxide on the silicon germanium layer; and forming a high dielectric constant layer of hafnium oxide on the silicon dioxide layer. The silicon germanium layer of Gate Stacks F-H comprised 25 wt %, 50 wt %, and 75 wt %, respectively, of germanium based on the total weight in the respective layer.

Figure 8:
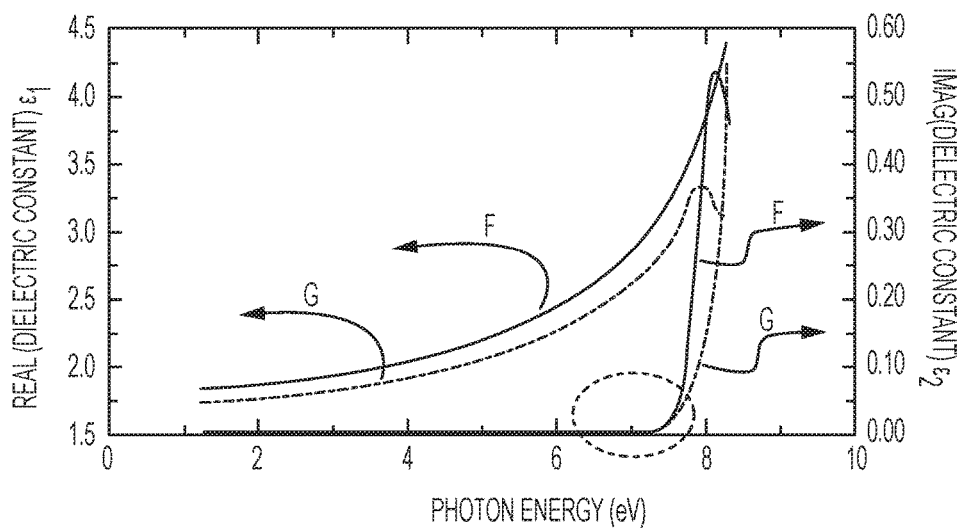
FIG. 8 is a graphical illustration of the real and imaginary parts of the dielectric function for the silicon germanium layers of Example 3 versus photon energy.
Figure 9:
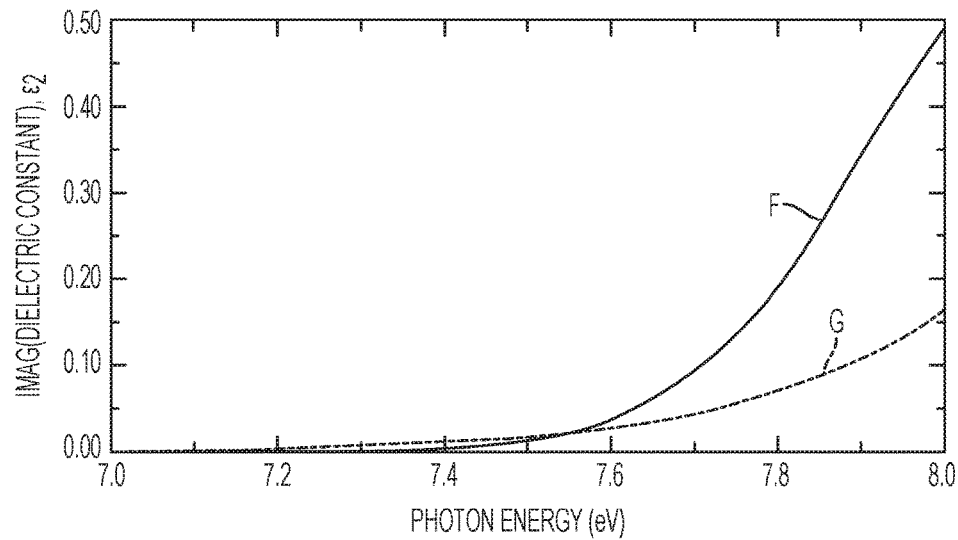
FIG. 9 is a graphical illustration of the imaginary parts of the dielectric function for the silicon germanium layers of Example 3 versus photon energy.
Figure 10:
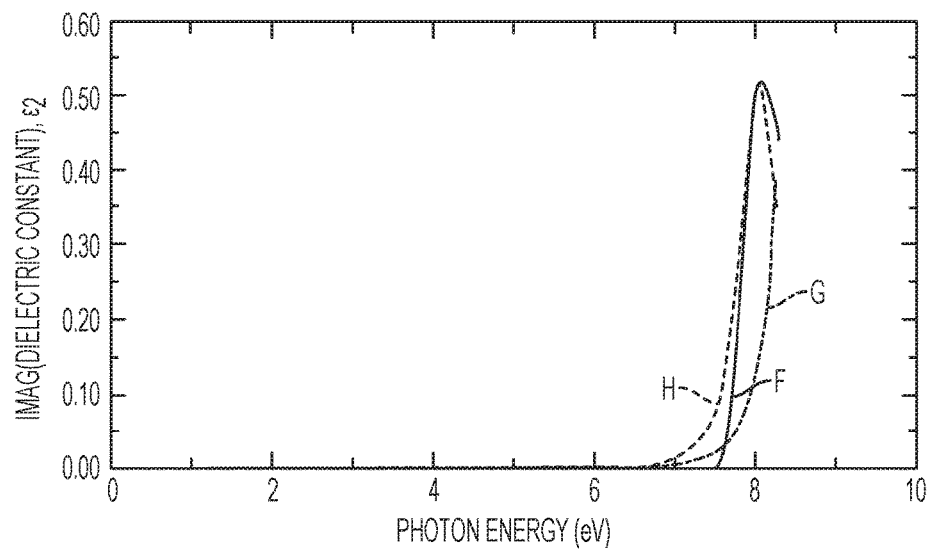
FIG. 10 is a graphical illustration of the imaginary parts of the dielectric function for the silicon germanium layers of Example 3 versus photon energy.

FIG. 8 is a graphical illustration of the real and imaginary parts of the dielectric function for the silicon germanium layers for Gate Stacks F and G versus photon energy. FIG. 9 and FIG. 10 are graphical illustrations of the imaginary parts of the dielectric function for the silicon germanium layers for Gate Stacks F-H capturing the band gap for the respective stacks. FIGS. 8-10 illustrate the shift that occurs as the concentration of the germanium increases.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e., occurrences) of the element or component. Therefore, "a" or "an" should be read to include one or at least one, and the singular word form of the element or component also includes the plural unless the number is obviously meant to be singular. "or" means "and/or".

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the disclosure and the practical application, and to enable others of ordinary skill in the art to understand the invention for various embodiments with various modifications as are suited to the particular use contemplated.

The diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of this disclosure.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It will also be understood that when an element, such as a layer, region, or substrate is referred to as being "on" or "over" another element, it can be directly on the other element or intervening elements may also be present. In contrast, when an element is referred to as being "directly on" or "directly over" another element, there are no intervening elements present.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   fitting a spectroscopic data of a first layer in a layered structure to a dielectric function ($\varepsilon$) having a real part ($\varepsilon_1$) and an imaginary part ($i\varepsilon_2$), the dielectric function ($\varepsilon$) having a formula:

$$\varepsilon = \varepsilon_1 \pm i\varepsilon_2;$$

repeating the fitting the spectroscopic data, or defining an n degree polynomial to the dielectric function;
   determining a second derivative and a third derivative of the n degree polynomial;
   equating the second derivative to a first governing equation and the third derivative to a second governing equation and determining a constant of the first governing equation and the second governing equation;
   based on the key governing equations, determining one or more of a band gap, a thickness, and a concentration of the first layer;
   repeating, simultaneously, for a second layer of the layered structure to determine one or more of a band gap, a thickness, and a concentration of the second layer;
   monitoring, by a fabricator, an unfinished product of the layered structure at various times for defects or process excursions; and
   taking, by the fabricator, a remedial action as necessary to address defects or process excursions prior to completion of a finished product.

2. The method of claim 1, wherein the layered structure comprises a gate stack.

3. The method of claim 2, wherein the gate stack comprises a substrate layer, a semiconductor layer, an oxide layer, and a high dielectric constant layer; wherein the semiconductor layer is located in between the substrate layer and the oxide layer and wherein the oxide layer is located in between the semiconductor layer and the high dielectric constant layer.

4. The method of claim 3, wherein the semiconductor layer comprises silicon, germanium, carbon, gallium, arsenide, indium, phosphorus, cadmium, or a combination comprising at least one of the foregoing.

5. The method of claim 4, wherein the semiconductor layer comprises silicon and germanium.

6. The method of claim 3, wherein the high dielectric constant layer comprises hafnium oxide.

7. The method of claim 1, wherein the fitting the spectroscopic data comprises fitting the spectroscopic data of two or more layers in the layered structure to two or more respective dielectric functions.

8. The method of claim 1, wherein the first governing equation has the formula (II).

9. The method of claim 1, wherein the second governing equation has the formula (III).

10. The method of claim 1, wherein the spectroscopic data comprises ultraviolet-visible-infrared spectroscopy data or ellipsometry data.

11. A system comprising:
    an illuminator that is operative to illuminate a layered structure over a spectral range to form an illuminated layered structure;
    a spectrometer that is operative to measure spectroscopic data from the illuminated layered structure; and
    a computer system configured to:
      receive the spectroscopic data from the spectrometer;
      fit the spectroscopic data of a first layer of the layered structure to a dielectric function ($\varepsilon$) having a real part ($\varepsilon_1$) and an imaginary part part ($i\varepsilon_2$), the dielectric function ($\varepsilon$) having a formula:

$$\varepsilon = \varepsilon_1 \pm i\varepsilon_2;$$

define an n degree polynomial to the dielectric function;
      determine a second derivative and a third derivative of the n degree polynomial;
      equate the second derivative to a first governing equation and equate the third derivative to a second governing equation; and determine a constant of the first governing equation and the second governing equation;
      based on one or both of the first governing equation and the second governing equation, determine one or more of a band gap, a thickness, and a concentration of the first layer;

repeat, simultaneously, for a second layer of the layered structure to determine one or more of a band gap, a thickness, and a concentration of the second layer; and monitor an unfinished product of the layered structure at various times for defects or process excursions, and send instructions to a fabricator to take remedial action as necessary to address defects or process excursions prior to completion of a finished product.

12. The system of claim 11, wherein the first governing equation has the formula (I).

13. The system of claim 11, wherein the second governing equation has the formula (II).

14. The system of claim 11, wherein the layered structure comprises a gate stack.

15. The system of claim 14, wherein the gate stack comprises one or both of a silicon germanium layer and a high dielectric constant layer.

16. A computer program product comprising a computer readable storage medium having program instructions embodied therewith, the program instructions executable by a processor to cause the processor to perform a method comprising:

fitting a spectroscopic data of a first layer in a layered structure to a dielectric function ($\varepsilon$) having a real part ($\varepsilon_1$) and an imaginary part ($i\varepsilon_2$), the dielectric function ($\varepsilon$) having a formula:

$\varepsilon = \varepsilon_1 \pm i\varepsilon_2$;

repeating the fitting the spectroscopic data, or defining an n degree polynomial to the dielectric function;

determining a second derivative and a third derivative of the n degree polynomial;

equating the second derivative to a first governing equation and the third derivative to a second governing equation and determining a constant of the first governing equation and the second governing equation;

based on the key governing equations, determining one or more of a band gap, a thickness, and a concentration of the layer;

repeating, simultaneously, for a second layer of the layered structure at various times for defects or process excursions prior to completion of a finished product; and monitoring an unfinished product of the layered structure at various times for defects or process excursions, and sending instructions to a fabricator to take remedial action as necessary to address defects or process excursions prior to completion of a finished product.

17. The computer program product of claim 16, wherein the first governing equation has the formula (I).

18. The computer program product of claim 16, wherein the second governing equation has the formula (II).

19. The computer program product of claim 16, wherein the layered structure comprises a gate stack.

20. The computer program product of claim 19, wherein the gate stack comprises one or both of a silicon germanium layer and a high dielectric constant layer.

* * * * *